(12) United States Patent
Weinberg et al.

(10) Patent No.: US 7,985,336 B2
(45) Date of Patent: *Jul. 26, 2011

(54) SYSTEMS, METHODS AND DEVICES RELATING TO A CELLULARIZED NEPHRON UNIT

(75) Inventors: Eli Weinberg, Needham, MA (US); Jeffrey T. Borenstein, Newton, MA (US)

(73) Assignee: The Charles Stark Draper Laboratory, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/851,050

(22) Filed: Aug. 5, 2010

(65) Prior Publication Data

US 2011/0024346 A1 Feb. 3, 2011

Related U.S. Application Data

(63) Continuation of application No. 11/541,275, filed on Sep. 28, 2006, now Pat. No. 7,790,028.

(60) Provisional application No. 60/721,632, filed on Sep. 28, 2005.

(51) Int. Cl.
*B01D 61/00* (2006.01)
*C12M 1/00* (2006.01)
*C12N 5/071* (2010.01)

(52) U.S. Cl. ............... 210/321.6; 210/483; 210/490; 210/500.21; 435/174; 435/176; 435/177; 435/180; 435/289.1; 435/297.1

(58) Field of Classification Search .............. 210/321.6, 210/483, 490, 500.21, 504, 506; 435/174, 435/176, 177, 180, 289.1, 297.1
See application file for complete search history.

(56) References Cited

U.S. PATENT DOCUMENTS

| | | | |
|---|---|---|---|
| 6,455,311 B1 | 9/2002 | Vacanti | |
| 6,942,879 B2 | 9/2005 | Humes | |
| 7,264,723 B2 * | 9/2007 | Singh et al. | 210/321.6 |
| 7,371,400 B2 * | 5/2008 | Borenstein et al. | 424/423 |
| 7,378,280 B2 * | 5/2008 | Quake et al. | 436/63 |
| 7,790,028 B1 | 9/2010 | Weinberg et al. | |
| 2002/0182241 A1 | 12/2002 | Borenstein et al. | |
| 2003/0003575 A1 | 1/2003 | Vacanti et al. | |
| 2003/0119184 A1 | 6/2003 | Humes | |
| 2005/0202557 A1 * | 9/2005 | Borenstein et al. | 435/369 |
| 2005/0238687 A1 | 10/2005 | Humes | |
| 2006/0136182 A1 | 6/2006 | Vacanti et al. | |
| 2007/0048727 A1 * | 3/2007 | Shuler et al. | 435/1.2 |
| 2007/0266801 A1 | 11/2007 | Khademhosseini et al. | |
| 2007/0281353 A1 * | 12/2007 | Vacanti et al. | 435/367 |
| 2008/0026464 A1 | 1/2008 | Borenstein et al. | |
| 2009/0101559 A1 * | 4/2009 | Bala Subramaniam et al. | 210/194 |
| 2009/0234332 A1 | 9/2009 | Borenstein et al. | |

OTHER PUBLICATIONS

Bourgeois et al., "Differentiated thick ascending limb (TAL) cultured cells derived from SV40 trangenic mice express functional apical NHE2 isoform: effect of nitric oxide," Eur. J. Physiol., 446:672-683 (2003).

Zhang et al., "Proliferation and osmotic tolerance of renal inner medullary epithelial cells in vivo and in cell culture," Am. J. Physiol Renal Physiol., 283:F302-F308 (2002).

Schumacher et al., "Advanced technique for long term culture of epithelia in a continuous luminal-basal medium gradient," Biomaterials, 23:805-815 (2002).

* cited by examiner

*Primary Examiner* — John Kim

(57) ABSTRACT

The present invention relates to bioartificial devices and systems that mimic kidney or nephron function and methods of making them.

22 Claims, 13 Drawing Sheets

Figure 1. Kidney with magnification of nephron

GEOMETRY OF LOOP OF HENLE DESCRIBED FOR NUMERICAL SIMULATION

PREDICTED PRESSURE DISTRIBUTION [Pa] IN LOOP OF HENLE STRUCTURE

PREDICTED NaCl CONCENTRATION [mmol/L] IN LOOP OF HENLE STRUCTURE

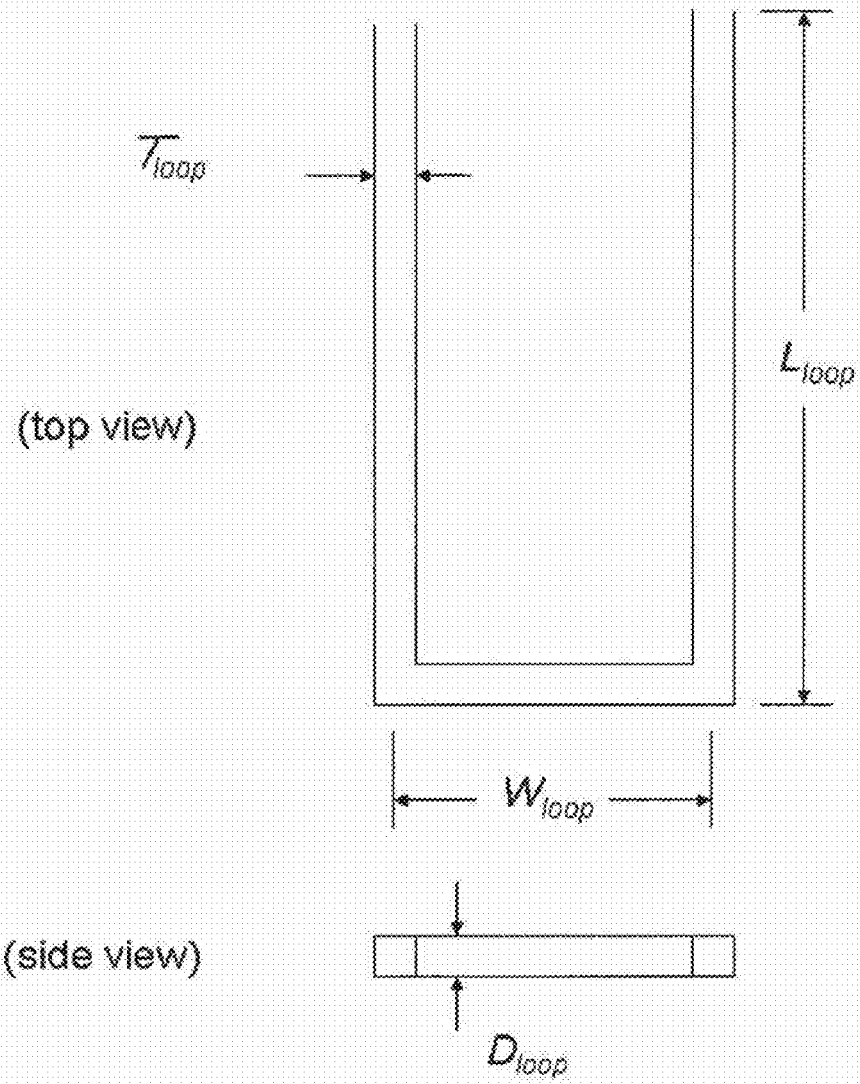
Figure 12. Dimension drawing for Loop of Henle structure
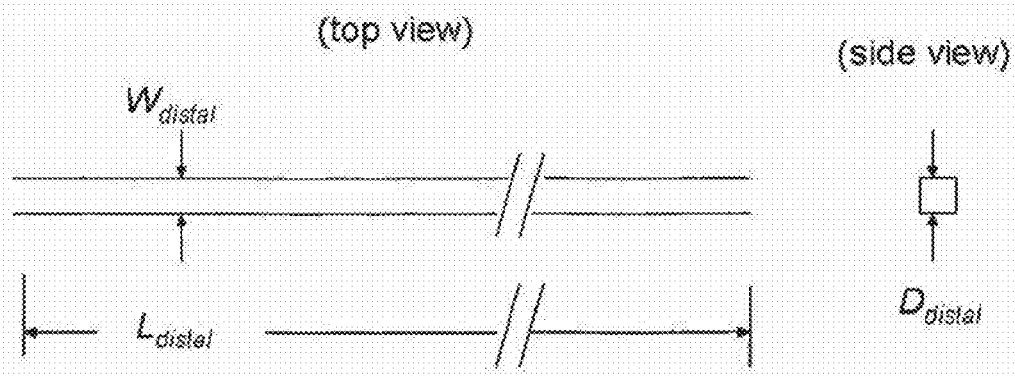
Figure 13. Dimension drawing for distal tubule structure

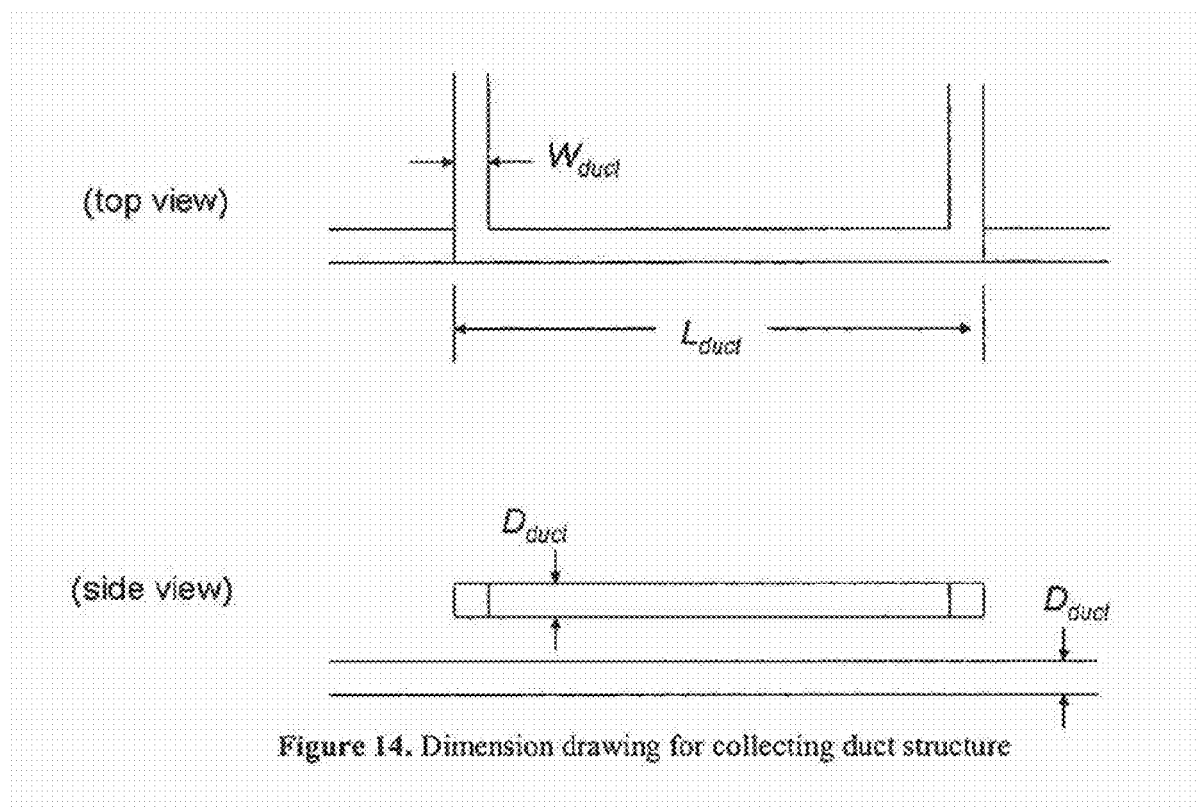
Figure 14. Dimension drawing for collecting duct structure

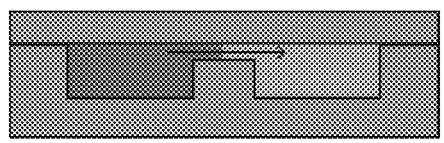
Figure 15A. Cross section of vessel with a "vertical pore". Arrow shows flow between vessels through the vertical pore.
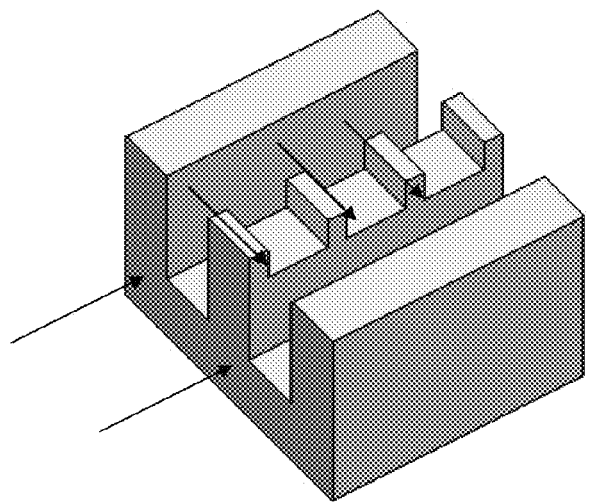
Figure 15B. 3D cutaway view of vertical pores. Flow through parallel vessels as shown follows the two-arrow direction, and flow through vertical pores as shown follows the three-arrow direction.

SYSTEMS, METHODS AND DEVICES RELATING TO A CELLULARIZED NEPHRON UNIT

CROSS REFERENCE TO RELATED APPLICATION

This application is a continuation of U.S. patent application Ser. No. 11/541,275 filed on Sep. 28, 2006, now U.S. Pat. No. 7,790,028, which claims priority to and the benefit of the filing date of U.S. Provisional Application No. 60/721,632, filed on Sep. 28, 2005, the content of which is incorporated by reference herein in its entirety.

FIELD OF THE INVENTION

The invention generally relates to microfabricated elements for replicating organ function in a mammal. In various embodiments, the invention more particularly relates to microfabricated elements for replicating kidney function in a human. According to various features, each microfabricated element replicates the function of a small volume of kidney tissue, and the elements are arrayed to form a device for replicating bulk kidney function.

BACKGROUND

A healthy kidney provides the vital function of clearing toxins from the blood and retaining everything else. The kidney achieves this essentially through a two-step process. First, the blood passes a mechanical filter. Cells and large solutes stay in the bloodstream while smaller solutes and a large portion of the plasma volume pass through the membrane. Second, cell-driven active transport and passive diffusion combine to create a re-absorption step, where almost all of the fluid and its constituents other than specific waste products, namely urea, are driven back into the bloodstream. The waste flows out as urine.

In a kidney, the two-step process is completed in millions of parallel units. Each unit functions independently of the others. In each unit, pressure-driven filtration takes place in a network of capillaries known as the glomerulus. The glomerulus is generally spherical and a few hundred microns in diameters. It is surrounded by Bowman's Capsule, which captures all materials that pass through the filter. Filtrate passes from there to the proximal tubule, Loop of Henle, distal tubule, and collecting duct, in that order. Active transport and diffusion take place in these systems. The process is highly efficient, excreting highly concentrated waste without loss of water or other vital blood components. The complete unit and accompanying blood vessels is known as the nephron.

Numerous conventional approaches for performing artificial mechanical filtration of blood exist. Once such approach is hemodialysis, which is widely used for treating patients with renal failure. In that approach, the patient's blood is caused to flow into a dialysis cartridge. The cartridge contains a porous membrane which allows only small particles to pass through. A fluid, known as the dialysate, is pumped through the device on the other side of the membrane from the blood. Small particles diffuse from the blood into the dialysate, which is discarded as waste.

Hemofiltration is a variation of hemodialysis. In this hemodialysis, blood is pumped through a dialysis cartridge. No dialysate is used. Blood plasma carrying small particles passes through the membrane and out of the device, and this fluid is discarded as waste. Combinations of hemofiltration and hemodialysis exist, where varying ratios of blood and dialysate are pumped through the cartridge.

Blood filtration can also be performed in a microfluidic device as described in U.S. Ser. No. 10/983,213 entitled "Micromachined Bilayer Unit of Engineered tissues," published as U.S. Patent Application Publication No. 20050202557. According to one approach disclosed in that application, a multi-layered micromachined device is constructed with a membrane similar to that of a dialysis cartridge, and filtration takes place between the layers of the device.

Another approach for filtering blood is disclosed in U.S. Ser. No. 10/316,000, entitled "Methods and Compositions of Bioartificial Kidney Suitable for Use In Vivo or Ex Vivo," publication as U.S. Patent Application Publication No. 20030119184. In this application, appropriate renal cells are grown on a hollow-fiber dialysis chamber and are shown to perform active transport. Such a device replicates the function of the renal proximal tubule, but does not replicate the elements beyond that in the filtrate flow path.

The approaches discussed above suffer from drawbacks. For example, they are not able to fully replicate nephron functions. More particularly, they are not able to replicate the nephron's function to form concentrated urine.

In hemodialysis, waste fluid is generated at approximately 500-700 milliliters per minute. In hemofiltration, waste fluid is generated at approximately 100 milliliters per minutes. As these procedures are performed for hours at a time, the patient is typically connected to a multi-gallon waste receptacle. The plasma fluid removed in hemofiltration must additionally be replaced, requiring more hardware and a reserve of plasma.

Existing bioartificial kidneys represent an improvement by reportedly re-absorbing 50% of the waste fluid. For comparison, a functioning kidney re-absorbs approximately 99% of fluid that leaves through the glomerulus. Without the ability to re-absorb a comparable percentage of fluid, existing approaches generate large amounts of waste, and therefore, are unlikely to lead to a useful wearable device.

Additionally, size-selective filtration performed by the approaches discussed above does not replicate selective filtration of the kidney and other cell-mediated metabolic functions. Survival rates and overall health of dialysis patients are poor in general, and this is attributed to dialysis not performing specific filtration and other kidney functions. Existing devices are thrombogenic so that Heparin or other anti-clotting agent are administered to the patient. There are numerous negative side effects to this treatment. Also, these systems typically require mechanical pumping to regulate the flows through the filter. Existing devices typically require pumping apparatus to drive blood (and dialysate, if appropriate) through the filtration.

Accordingly, there is a need for an improved approach that can more fully replicate kidney function. More specifically, there is a need for an approach that can more fully replicate nephron's formation of concentrated urine.

BRIEF DESCRIPTION OF THE INVENTION

In various embodiments, the invention addresses the deficiencies in the art by providing improved systems, methods and devices relating to microfabricated, cellularized elements for replicating kidney function in a human. According to various configurations, the microfabricated elements of the invention each replicates the function of a small volume of kidney tissue. The elements may be arrayed to form a device/system for replicating bulk kidney function. According to one embodiment, each element includes portions for replicating or mimicking the function of the Loop of Henle, distal tubule, and collecting duct. According to one feature, the microfabricated, cellularized device of the invention more fully replicates the steps that take place in the nephron. According to another feature, the microfabricated, cellularized device of the invention replicates all or substantially all of the steps that take place in the nephron. In one embodiment, a pressure gradient is introduced across a mechanical filter to replicate the filtration step found in a kidney glomerulus. Cellularized, diffusion-scale loops replicate the re-absorption steps. According to one application, the invention may be employed to create a single functional element for experimentally replicating nephron function, for example, for studying kidney function. In another application, a device according to the invention including a plurality of elements employed in parallel, is used to replace lost renal function in patients with kidney failure, as an alternative to other renal disease therapies. In a further application, the elements and devices/systems of the invention may be employed to form wearable blood filters as an alternative to conventional dialysis machines.

A first aspect of the invention relates to a bioartificial device comprising a cellularized, microfabricated loop mimicking the functionality of the Loop of Henle.

In certain embodiments, the cellularized, microfabricated loop includes a blood flow layer having a first microfluidic channel formed therein. The loop further includes a filtrate layer coupled to the blood flow layer through a first membrane positioned between the blood flow layer and the filtrate layer. The blood flow layer may further include a blood inlet. In certain embodiments, the filtrate layer includes a generally u-shaped microfluidic channel formed therein, and the filtrate layer may further include a filtrate inlet.

In certain configurations, the first microfluidic channel of the loop includes an ascending limb and a descending limb. In certain embodiments, a porous medium is deposited between at least a portion of the ascending limb and the descending limb of the first microfluidic channel. The porous medium may include one or more vertical pores. Alternatively, the porous medium may be formed with one or more hollow fibers.

In certain configurations, the generally u-shaped microchannel of the loop includes an ascending limb and a descending limb. In certain embodiments, a plurality of water-permeable cells are positioned within the descending limb of the generally u-shaped microfluidic channel. In certain embodiments, a plurality of salt-pumping cells are positioned within the ascending limb of the generally u-shaped microfluidic channel.

In certain embodiments, the bioartificial device further includes a component that mimics the functionality of a collecting duct, and that component also includes a blood flow layer having a first microfluidic channel formed therein, and a collecting duct filtrate layer having a second microfluidic channel formed therein, and a second porous membrane positioned between the collecting duct blood flow layer and the collecting duct filtrate layer. The collecting duct filtrate layer may also include a filtrate outlet. In certain embodiments, a plurality of water-permeable cells are positioned within the collecting duct filtrate layer.

In certain embodiments, the bioartificial device further includes a component that mimics the functionality of a distal tubule, and that component also includes a distal tubule blood flow layer having a first microfluidic channel formed therein, and a distal tubule filtrate layer having a second microfluidic channel formed therein, and a third porous membrane positioned between the distal tubule blood flow layer and the distal tubule filtrate layer. In certain embodiments, the first and second microfluidic channels of the distal tubule component have a generally serpentine configuration. In certain embodiments, a plurality of water-permeable cells are positioned within the distal tubule filtrate layer. In specific embodiments, the distal tube component provides for diffusion of water from the second microchannel across the third porous membrane into the first microchannel.

In certain embodiments, the bioartificial device comprises microchannels which lie in substantially one plane. In certain embodiments, the microchannels carrying the blood flow are separate from the microchannels carrying the filtrate flow, and such separation can be through forming the microchannels with hollow fibers or using porous membrane or other porous medium.

Accordingly, the invention provides a bioartificial device that mimics the function of a nephron unit.

A second aspect of the invention relates to a bioartificial system including a plurality of a bioartificial device or unit described herein. The bioartificial system can replicate the functionality of a kidney. The unit may include a first set of microchannels formed thereon; a second set of microchannels; and a semi-permeable membrane defining a first surface and a second surface, wherein the first surface of the membrane is secured adjacent to a surface of the first set of microchannels and the second surface of the membrane is secured adjacent to a surface of the second layer. In certain embodiments, a first portion of the first set of the microchannels include water-permeable cells and a second portion of the first set of the microchannels include salt-pumping cells. In certain embodiments, the first set and second set of microchannels are on a first layer and a second layer, respectively. In alternative embodiments, he first set and second set of microchannels are on two separate layers coupled through the semi-permeable membrane.

A third aspect of the invention relates to methods for making the devices and systems described herein. Methods of using the devices and systems are also provided, including, but not limited to, "lab-on-a-chip" type of research uses as well as clinical or therapeutic uses.

In certain embodiments, the invention provides a bioartificial loop that replicates a function of the Loop of Henle. The artificial loop is microfabricated and cellularized. In specific embodiments, the bioartificial loop has a descending limb seeded or cellularized with water-permeable cells. In specific embodiments, the bioartificial loop has an ascending limb seeded or cellularized with salt-pumping cells. A bioartificial loop of the invention may replicate a function of the Loop of Henle at a level that is about 10%, 20%, 30%, 40%, 50%, 60%, 70%, 80% 90%, 100% or even greater than the function level of the Loop of Henle in a nephron unit in a normal subject. Depending on the intended uses, the normal subject may be an animal or a human subject free or substantially free of any kidney impairments, diseases or conditions.

In certain embodiments, the invention provides a bioartificial device that replicates the function of a nephron unit, which device comprises a bioartificial loop of the invention. In certain embodiments, the bioartificial device further comprises a bioartificial distal tubule. In certain embodiments, the bioartificial device further comprises a bioartificial collecting duct. In certain embodiments, the bioartificial device also comprises components that replicate the function of the blood vessels associated with a nephron unit. In certain embodiments, the bioartificial device comprises a countercurrent re-absorption system.

A bioartificial device of the invention may replicate a function of a nephron unit at a level that is about 10%, 20%, 30%, 40%, 50%, 60%, 70%, 80% 90%, 100% or even greater than the function level of a nephron unit in a normal subject. Depending on the intended uses, the normal subject may be an animal or a human subject free or substantially free of any kidney impairments, diseases or conditions.

In further embodiments, the invention provides a bioartificial system comprising a plurality of a bioartificial device of the invention. In certain embodiments, a bioartificial system of the invention may comprise at least 1, 10, 100, 1000, 10000, 50000, 100000, 200000, 500000, 800000, 1000000, or even greater bioartificial devices of the invention. In specific embodiments, the bioartificial system replicates kidney function at a level that is about 10%, 20%, 30%, 40%, 50%, 60%, 70%, 80% 90%, 100% or even greater than the function level of a kidney in a normal subject. Depending on the intended uses, the normal subject may be an animal or a human subject free or substantially free of any kidney impairments, diseases or conditions.

The invention may employ different tests to evaluate kidney function level and the function level of the subject bioartificial devices and their components. An example of such tests may include glomerular filtrate rate (GFR) determination based on creatine measurement, which is a calculation of how efficiently the kidneys are filtering wastes from the blood.

In certain embodiments, a bioartificial system of the invention is suitable for being implanted into a subject patient. The subject patient may be a patient having a kidney disease, for example, one that requires frequent dialysis. A bioartificial system of the invention may substitute for a kidney transplant.

In alternative embodiments, a bioartificial system of the invention is designed for excorporeal use by a patient in need thereof. For example, the bioartificial system may include or be connected with other components that allow a subject patient to wear the system in physical proximity.

Another aspect of the invention relates to methods for making the bioartificial loops, devices, and systems of the invention.

Other systems, methods, devices, aspects, applications and features of the invention are described below with reference to the drawings.

BRIEF DESCRIPTION OF THE DRAWINGS

The foregoing discussion will be understood more readily from the detailed description of the invention with reference to the following drawings:

FIG. 12 is a dimensioned drawing for a microfabricated bioartificial Loop of Henle structure according to an illustrative embodiment of the invention.

FIG. 13 is a dimensioned drawing for a microfabricated bioartificial distal tubule structure according to an illustrative embodiment of the invention.

FIG. 14 is a dimensioned drawing for a microfabricated bioartificial collecting duct structure according to an illustrative embodiment of the invention.

FIG. 15A is a schematic of a vertical pore or vertical link connecting two microchannels.

FIG. 15B is a schematic of vertical pores connecting two microchannels.

DETAILED DESCRIPTION OF ILLUSTRATIVE EMBODIMENTS

Overview

Figure 1:
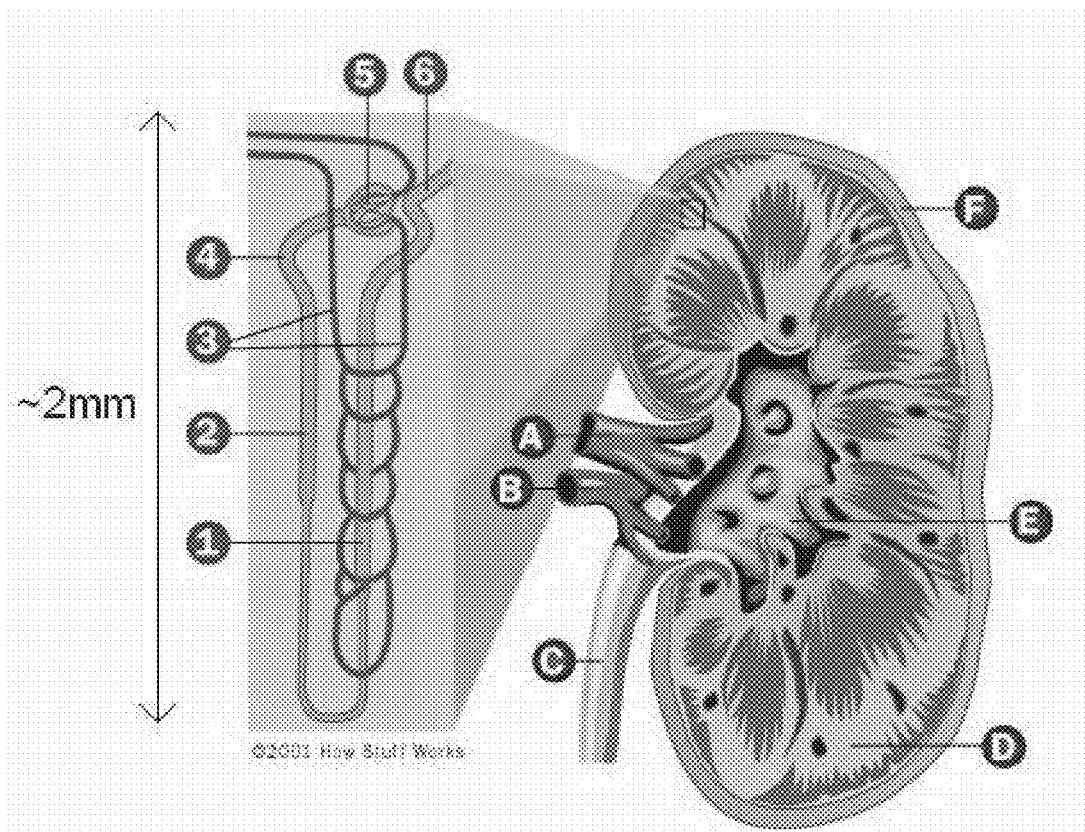
FIG. 1 depicts a cross-section of a human kidney with magnification of nephron.

According to various illustrative embodiments, the invention addresses the deficiencies in the art by creating a bioartificial device that replicates or substantially replicates the function of the Loop of Henle, distal tubule, collecting duct, and associated blood vessels. This system is referred to herein as the countercurrent re-absorption system. According to one feature, the countercurrent re-absorption system allows for the formation of highly concentrated urine and little waste product. According to one feature, the flow behavior of the system is controlled so that no mechanical pumps are needed. According to another feature, the invention enables the fabrication of a system that fully or substantially fully mimics physiological kidney function or a microdevice that fully or substantially fully mimics the function of a nephron unit. FIG. 1 illustrates the geometry and scale of a nephron unit.

One difference between the approaches of the countercurrent re-absorption system and former filtration approaches is the use of a combination of cultured renal epithelial cells and microfabrication to create an artificial Loop of Henle, as well as other components of a nephron unit. The Loop of Henle creates concentrated urine by cycles of cell-mediated pumping and diffusion. Since diffusion typically occurs at micronscale lengths, the Loop of Henle can suitably be manufactured using microfabrication technology. Cells introduced to the microfabricated Loop of Henle (and optionally additionally, other microfabricated components of a bioartificial nephron unit) perform the pumping and metabolic functions of a healthy nephron. Additionally, according to one feature, incorporation of endothelial cells reduces thrombogenicity of the device.

According to one embodiment, the bioartificial countercurrent re-absorption system is produced in three steps. First, the device is designed based on a theoretical understanding of natural kidney function. Second, the device is fabricated using techniques common to micro-electro-mechanical systems (MEMS) fabrication. Third, the device is seeded with cells.

According to one approach, the invention employs a mathematical model for creating a device that delivers the desired mass transport. According to this approach, software simulates the movement of fluids and molecules in a given microfluidic device. Dimensions for the device are chosen, appropriate mass transport constants are inserted into the model, and predictions about desired transport features are made. Dimensions are determined for each unit of the device based on published mass transport values.

The diffusivities of urea and NaCl in the blood and filtrate are well-known diffusivities of those solutes in water. According to one embodiment, a semi-permeable or porous membrane having hydraulic permeability of about 31 ml/h/m$^2$/mmHg, matching that of membranes used in existing bioartificial kidney systems is incorporated into the devices and systems herein. The distal tubule and collecting duct can be lined with cells to allow for transport of water and blocks all other transport, thus mimicking the function of the distal tubule of a kidney. Similarly, the devices and systems may include components that are cellularized with a plurality of water-permeable cells, thus mimicking the function of the collecting duct of a kidney.

Devices and Systems of the Invention

Accordingly, the invention provides various microfabricated devices and systems that mimic the function of one or more nephron units and a kidney, preferably, a human kidney. In certain embodiments, the devices and systems are cellularized and include renal epithelial cells, such as for example, water-permeable cells and salt-pumping cells. In certain embodiments, the devices and systems are vascularized and include vascular cells, such as for example, endothelial cells.

Certain embodiments contemplate a microfabricated system that can replicate kidney function and are implantable into a subject patient. Such implantable systems preferably operate under a regulated pressure gradient such that after implantation, the subject patient's blood pressure remains substantially un-disturbed. In a natural kidney, blood flowing through the renal artery is distributed via a series of divisions and ends by feeding the glomeruli through the afferent arterioles. After passing through the glomerular capillaries, blood leaves through the efferent arterioles to enter a second capillary network, the peritubular capillaries, which surround the tubules and then leave via renal venules. Each of these capillary networks serves the functional needs of the kidney. Every day 180 liters of fluid pass through the glomerular capillaries as filtrate. About 99% is recovered from the tubules and carried back into the general circulation via the peritubular capillaries. The remaining 1% continues on to its final presentation as urine. It is well known that a pressure gradient exists through this vascular system. The pressure profile along the intrarenal vasculature starts with a mean arterial pressure of 100 mm Hg, and significantly drops between the renal artery and the glomerular capillaries. This is due to the pre-glomerular resistance of the afferent arteriole. The glomerular capillary pressure is much higher than any other capillary bed in the body (60 vs. 13 mm Hg). The increased hydrostatic pressure is a necessary phenomenon to insure the generation of filtrate and hence the glomerular filtration rate (GFR). A second resistance site is postglomerular and is located at the outflow site of the glomerulus in the efferent arterioles. The third site is the venous resistance located after the peritubular capillaries and most likely at the arcuate and interlobar veins. The postglomerular or efferent arteriolar resistance also serves to maintain glomerular pressure and, in turn, is responsible for the pressure drop from the glomerular capillaries to the peritubular capillaries. Peritubular capillary pressure is regulated at around 15-20 mm Hg. The kidney itself continuously regulates distribution of flow within the renal tissue. This process is called autoregulation and is responsible for maintaining intra-renal blood flow over a wide range of systemic perfusion pressures. Accordingly, a system of the invention, by itself, or coupled with other biological or bioartificial systems, preferably mimics the autoregulation of a natural kidney.

In alternative embodiments, the devices and systems of the invention are intended for excorporeal uses.

Integrated Device

Figure 2:
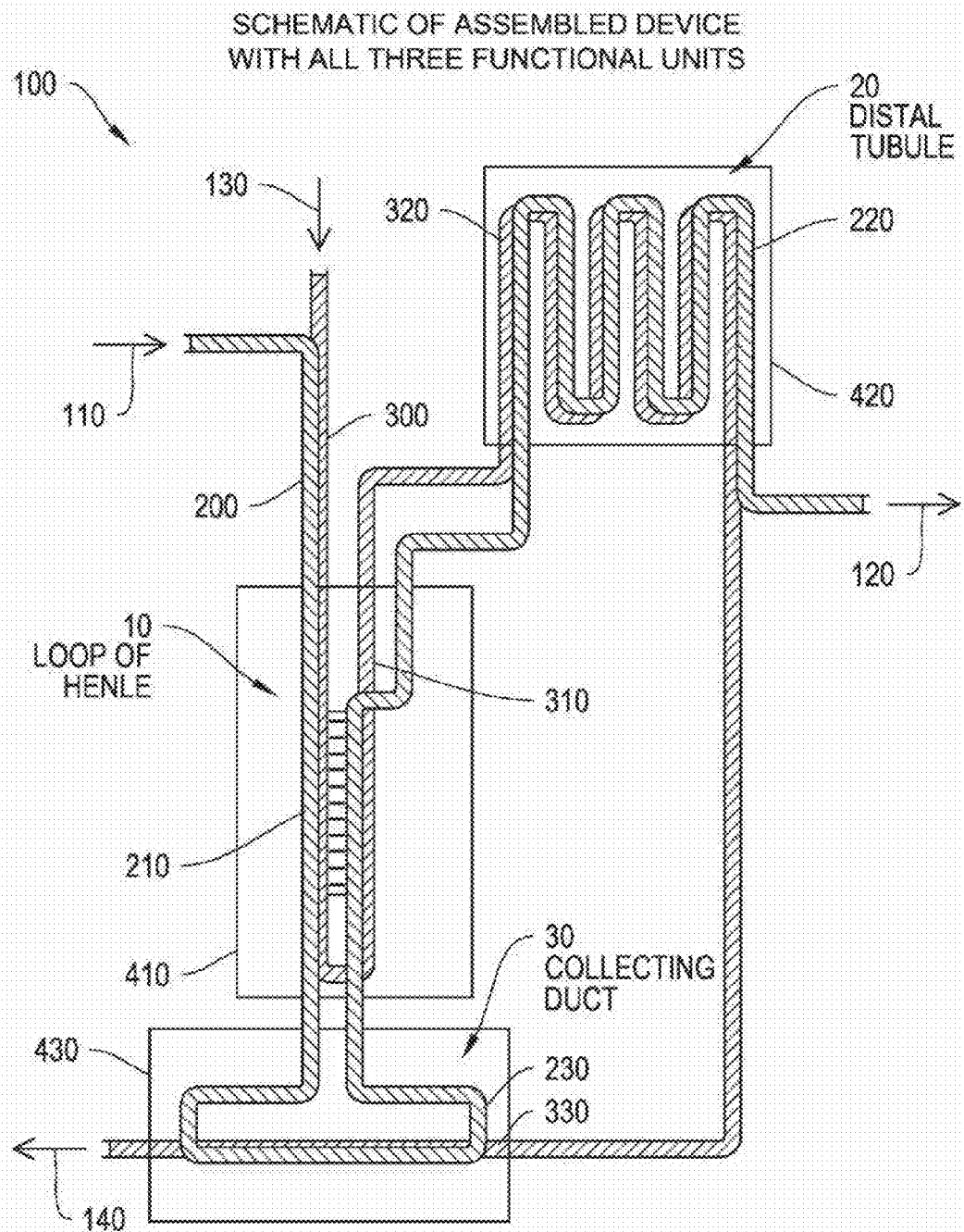
FIG. 2 is a schematic of an assembled integrated device including a microfabricated bioartificial Loop of Henle, distal tubule and collecting duct according to an illustrative embodiment of the invention.

In a kidney, blood is first filtered through glomeruli, and the filtrate flows out of the glomerulus and into the proximal tubule, then into the Loop of Henle, then into the distal tubule and collecting duct. According to one implementation, the bioartificial components of the invention are used to replace the Loop of Henle, distal tubule, and collecting duct, with another suitable system (either biological or bioartificial) supplying the functions of the glomerulus and proximal tubule. FIG. 2 shows a schematic of an illustrative integrated device according to this implementation. As shown, the device 100 of FIG. 2 includes a bioartificial loop 10 that mimics the function of the Loop of Henle, distal tubule 20 and collecting duct 30, all interconnected to replace their biological counterparts.

As illustrated, the device 100 comprises a blood flow layer 200 and a filtrate layer 300, and a membrane positioned inbetween the two layers 200 and 300. The blood flow layer 200, as shown, includes a blood flow layer 210 of the loop 10, a blood flow layer 230 of the collecting duct 30 and a blood flow layer 220 of the distal tubule 20; the three component blood flow layers 210, 220, and 230 of the blood flow layer 200 lie in substantially one plane. In alternative embodiments, the component blood layers 210, 220, and 230 form a substantially three-dimensional network or lie in substantially two or more planes. The blood flow layer 200 further comprises microfluidic channels or microchannels formed therein, which allow blood flow from the blood inlet 110 into the device 100 and out of the device through the blood outlet 120.

As illustrated, the device 100 comprises a filtrate layer 300 also including three components, a filtrate layer 310 of the loop 10, a filtrate layer 330 of the collecting duct 30, and a filtrate layer 320 of the distal tubule 20. Similarly, these component filtrate layers may lie in the same plane or in multiple planes. Similarly, these component filtrate layers may form a substantially three-dimensional network. The filtrate layer 300 further comprises microfluidic channels or microchannels formed therein, which allow filtrate flow from the filtrate inlet 130 into the device 100 and out of the device through the filtrate outlet 140.

In certain embodiments involving three-dimensional microfluidic networks, vertical links or vertical pores are employed to put the different layers in the networks in fluid communication with each other. A "vertical link" or "vertical pore" generally refers to a partial or complete through hole that vertically connects one microchannel in one layer to at least another microchannel in the same or a second layer. Vertical links are generally substantially perpendicular to the layers or the microchannels which they connect. Hollow fibers can be incorporated into the devices and systems to form such vertical pores.

Also as illustrated, the device 100 comprises a membrane. The membrane includes three components, the membrane 410 of the loop 10, the membrane 420 of the distal tubule 20, and the membrane 430 of the collecting duct 30. Each of the component membranes 410, 420, 430, is positioned inbetween its respective component blood flow layer and component filtrate layer. As illustrated, the component membranes 410, 420, and 430 are separate from each other. In alternative embodiments, the component membranes 410, 420, and 430 may be part of a single piece of membrane.

As shown, the membrane and its components have an upper surface that is exposed to the blood flow layer 200, and a lower surface that is exposed to the filtrate layer 300.

In certain embodiments, the membrane and its components are semi-permeable. Preferably, the pore size of the membrane is smaller than the cell diameters such that cells are not able to pass through (i.e., a low permeability for animal cells), while low molecular weight nutrients and fluids can pass through (i.e. a high permeability for nutrients). Cell sizes vary but in general, they are in the range of microns. In certain embodiments, the membrane is made of a hemocompatible material. Preferably, the average membrane pore size is on a submicron-scale to ensure effective screening of the cells. Semi-permeable membranes include a wide array of different membrane types and morphologies, which can be classified as follows: (1) Track-etch membranes consisting of cylindrical through-holes in a dense polymer matrix, typically made by ion-etching; or (2) Fibrous membranes made by various deposition techniques of polymeric fibers. While these membranes do not have a well-defined pore topology, production methods have been sufficiently refined so that fibrous membranes have specific molecular weight cut-offs. Track-etch type membranes are preferred, as they limit the fluid motion in one dimension. Preferably, fluid motion is in the vertical direction. Fibrous membranes permit fluid motion both laterally and vertically.

Any suitable approach, including those known in the art and those described in the cited U.S. patents and patent applications, such as U.S. Pat. Nos. 6,942,879; 6,455,311, and U.S. Patent Application Publication Nos. 20060136182, 20050238687, 20050202557, 20030003575, 20020182241, as well as other references, may be employed to provide suitable porous membranes.

Loop of Henle

Figure 3:
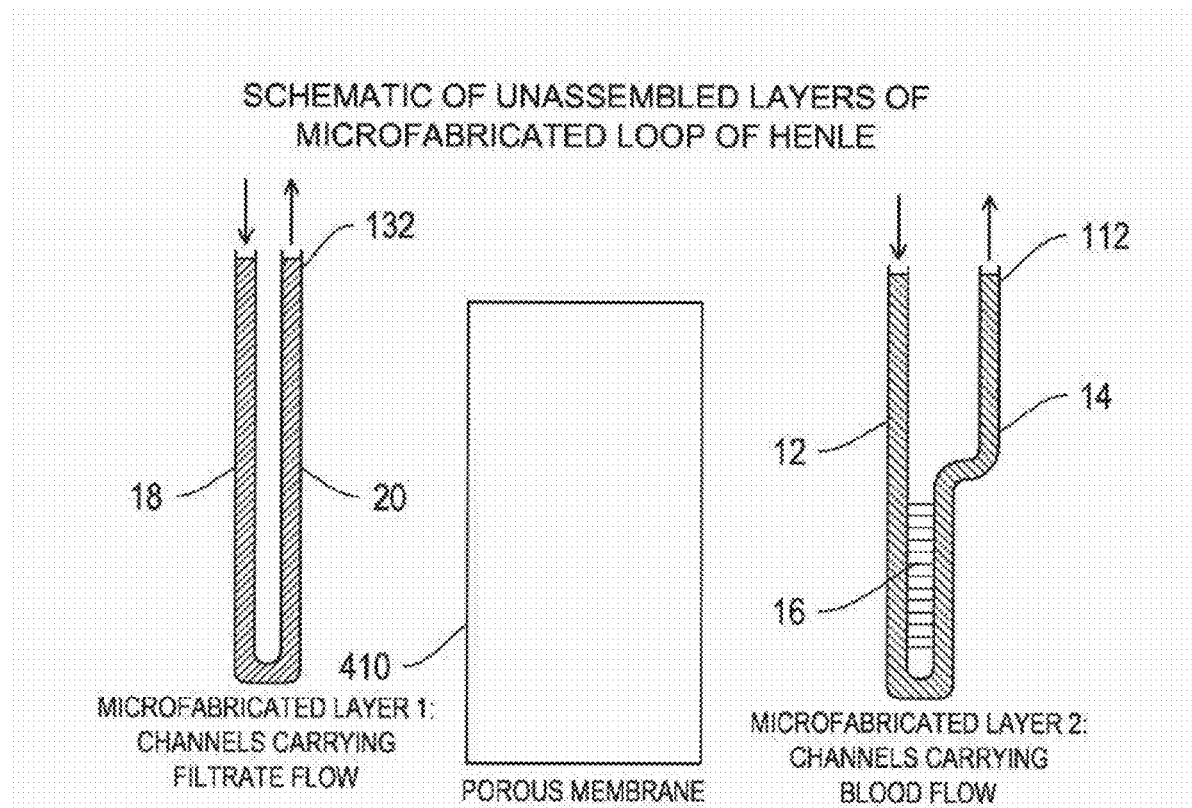
FIG. 3 is a schematic of unassembled layers of a microfabricated bioartificial Loop of Henle according to an illustrative embodiment of the invention.
Figure 6:
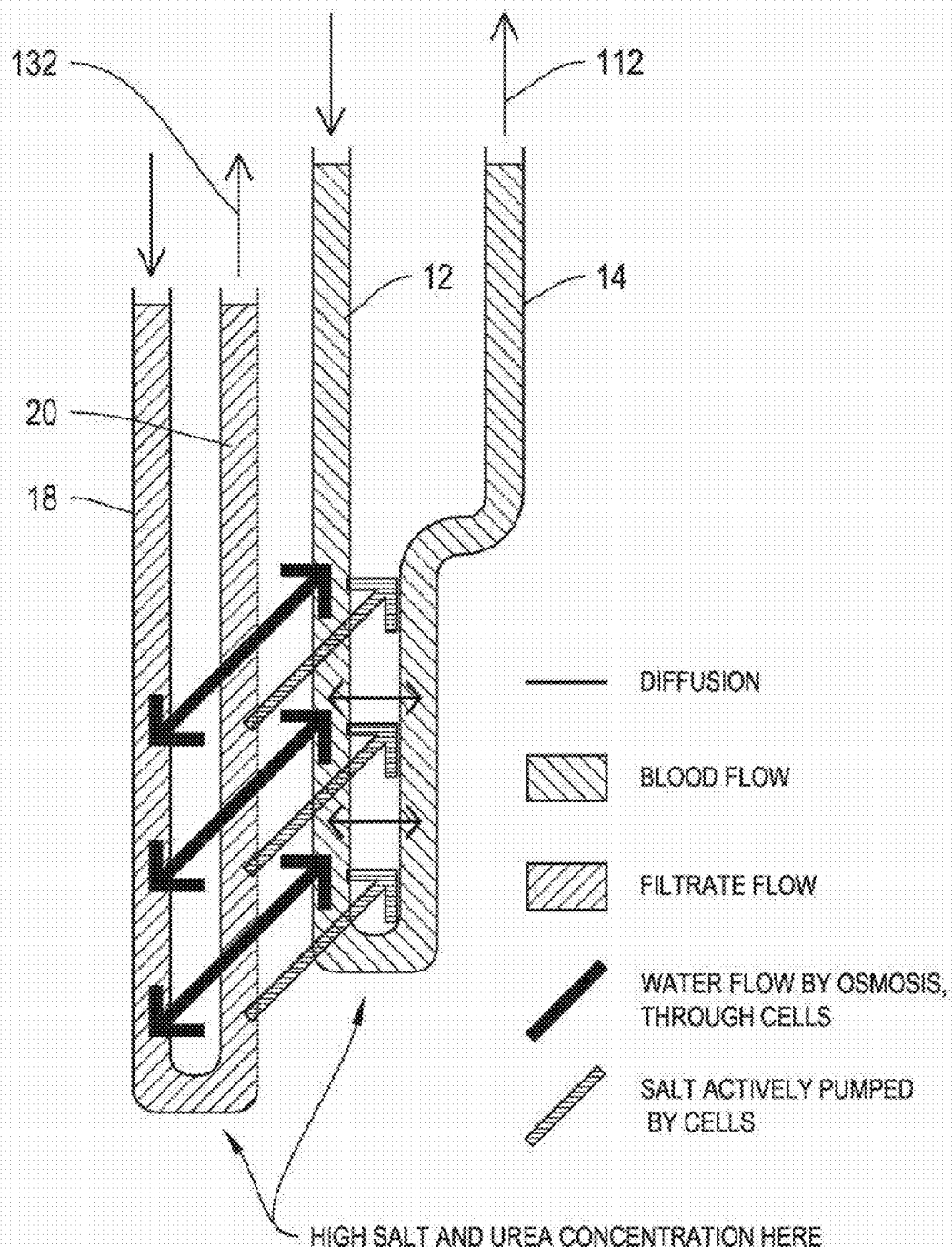
FIG. 6 is a schematic of flow behaviors in a microfabricated bioartificial Loop of Henle according to an illustrative embodiment of the invention.

An essential function of the Loop of Henle is to create high concentrations of urea, salt, and other solutes. Illustrated in FIG. 1, the Loop of Henle, as found in nature, typically consists of a U-shaped tubule carrying filtrate with blood vessels following its course. A bioartificial loop that mimics the function of the Loop of Henle according to an illustrative embodiment of the invention is depicted in FIG. 3. The illustrative bioartificial Loop of Henle 10 shown in FIG. 3 includes a substantially u-shaped microfluidic channel having a descending limb 18 and an ascending limb 20 formed in the corresponding filtrate layer 310 to carry filtrate flow from the filtrate inlet 130 through the outlet 132. In addition, the bioartificial loop 10 includes a bioartificial blood vessel also comprising a descending limb 12 and ascending limb 14 formed in the corresponding blood flow layer 210 to carry blood flow from the blood inlet 110 through the outlet 112. A porous medium 16 positioned between a substantial portion of the limbs 12 and 14 allows diffusion between the two limbs 12 and 14 of the blood flow layers. In certain embodiments, the porous medium 16 can be formed as one or more vertical pores connecting the limbs 12 and 14, such as for example, the vertical pore schematics illustrated in FIGS. 15A and 15B. Alternatively, the porous medium 16 can be formed by incorporating hollow fibers into the device to allow for communication between the limbs 12 and 14. Communication between the two limbs 12 and 14 contributes to the countercurrent system of the blood flow layer 210 to create high-concentration blood at the tip 28 of the microchannel of the blood flow layer 210 as shown in FIG. 6.

Figure 5:
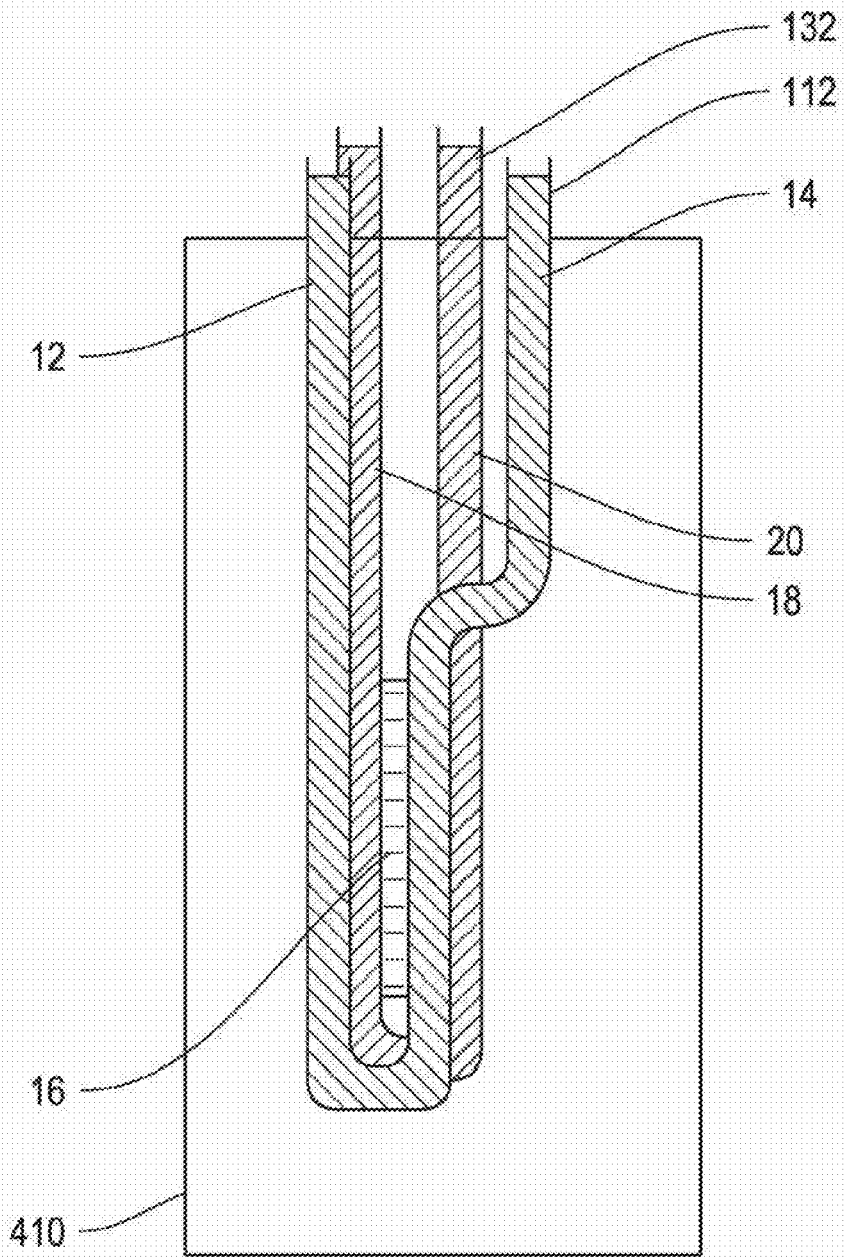
FIG. 5 is a schematic of assembled layers of a microfabricated bioartificial Loop of Henle according to an illustrative embodiment of the invention.

In preferred embodiments, a single bioartificial blood vessel is coupled with a substantially u-shaped tubule as shown in FIG. 5 through the loop membrane 410 to make the bioartificial Loop of Henle 10.

As shown in FIGS. 3 and 5, according to the illustrative embodiment, this bioartificial Loop of Henle 10 is formed on two microfabricated layers 210 and 310 separated by a water- and protein-permeable (porous) membrane 410. As shown in FIG. 6, glomelular filtrate circulates in one layer (filtrate layer 310) and blood in the other (blood flow layer 210).

Figure 4:
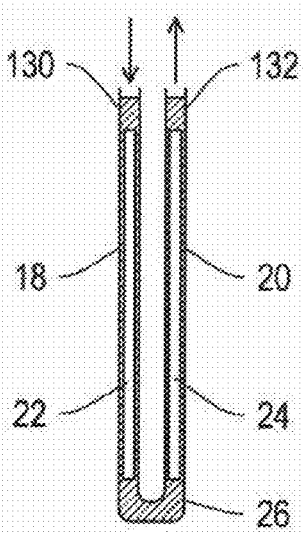
FIG. 4 is a schematic of cells seeded in a filtrate layer of the microfabricated bioartificial Loop of Henle of FIG. 2 according to an illustrative embodiment of the invention.

The bioartificial loop 10, in particular, the substantially u-shaped microchannel in the filtrate layer 310 may further include a plurality of renal epithelial cells as shown in FIG. 4. The descending limb 18 includes or is lined with cells 22 that generally permit water to pass through and little else. The ascending limb 20 is lined with cells 24 that pump NaCl out of the tubule or microchannel and generally do not allow water to pass. These are also generally referred to as water-permissive or permeable and salt-pumping cells, respectively. Specific examples of such cells are described below. According to one feature, the actions of pumping salt out of the ascending tubule and circulating flow by having correctly permeable walls of the microchannels creates a countercurrent multiplier. In such an arrangement, the concentration of solutes at the tip 26 of the u-shape becomes much higher than the concentration at the inlet 130 and outlet 132. In particular embodiments, the substantially u-shaped microchannel has different depths or diameters where the microchannel has a substantially cylindrical shape. For example, the ascending limb 20 may be thicker than the descending limb 18. In a specific embodiment, the ascending limb 20 has a substantially cylindrical shape and a diameter of about 60 microns, and the descending limb 18 has a substantially cylindrical shape and a diameter of about 12 microns.

The salt-pumping cells in a biological or natural Loop of Henle are thought to be typically less powerful than those found in the renal proximal tubule. According to one approach, cells pumping NaCl at 10%, 20%, 30%, 40%, 50%, 60%, 70%, 80%, or 90% of the conventionally accepted rate of renal proximal tubule cells are selected to be included in the ascending limb 20 of the bioartificial loop 10. Thus, they pump $Na^+$ at a rate of $1.6 \times 10^{-6}$ mmol/s/cm$^2$ or higher.

Thus, according to one illustrative embodiment, an artificial Loop of Henle structure of the invention includes a microchannel with an ascending limb lined with cells that actively transport $Na^+$ at about $1.6 \times 10^{-6}$ mmol/s/cm$^2$ and block other transport, and a descending limb lined with cells that allow transport of water and block or substantially block the transport of most, if not all, other species (including protein and other molecules in the filtrate).

Figure 9:
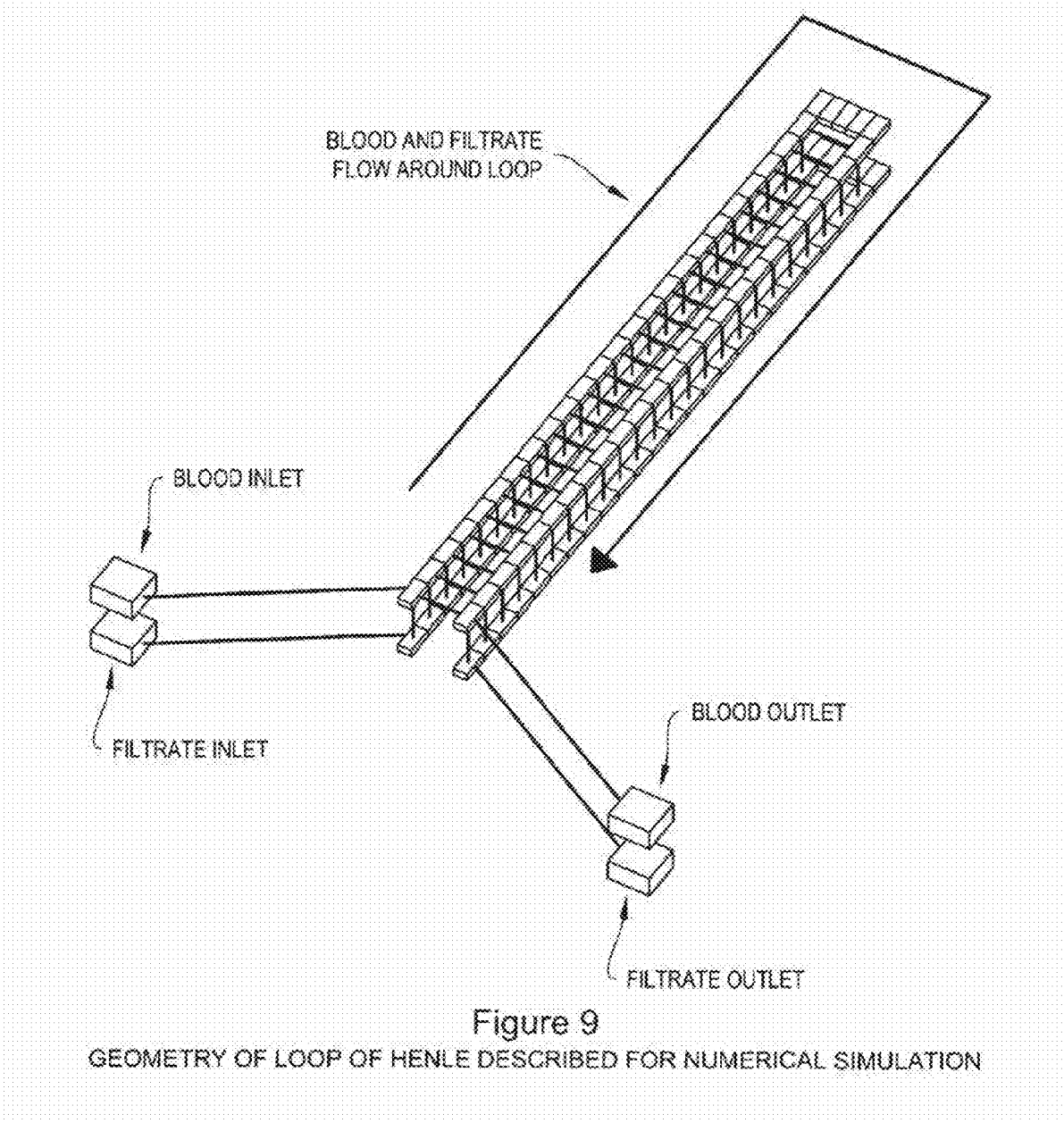
FIG. 9 shows a schematic of a geometry of a microfabricated bioartificial Loop of Henle described for numerical simulation of an illustrative embodiment of the invention.
Figure 10:
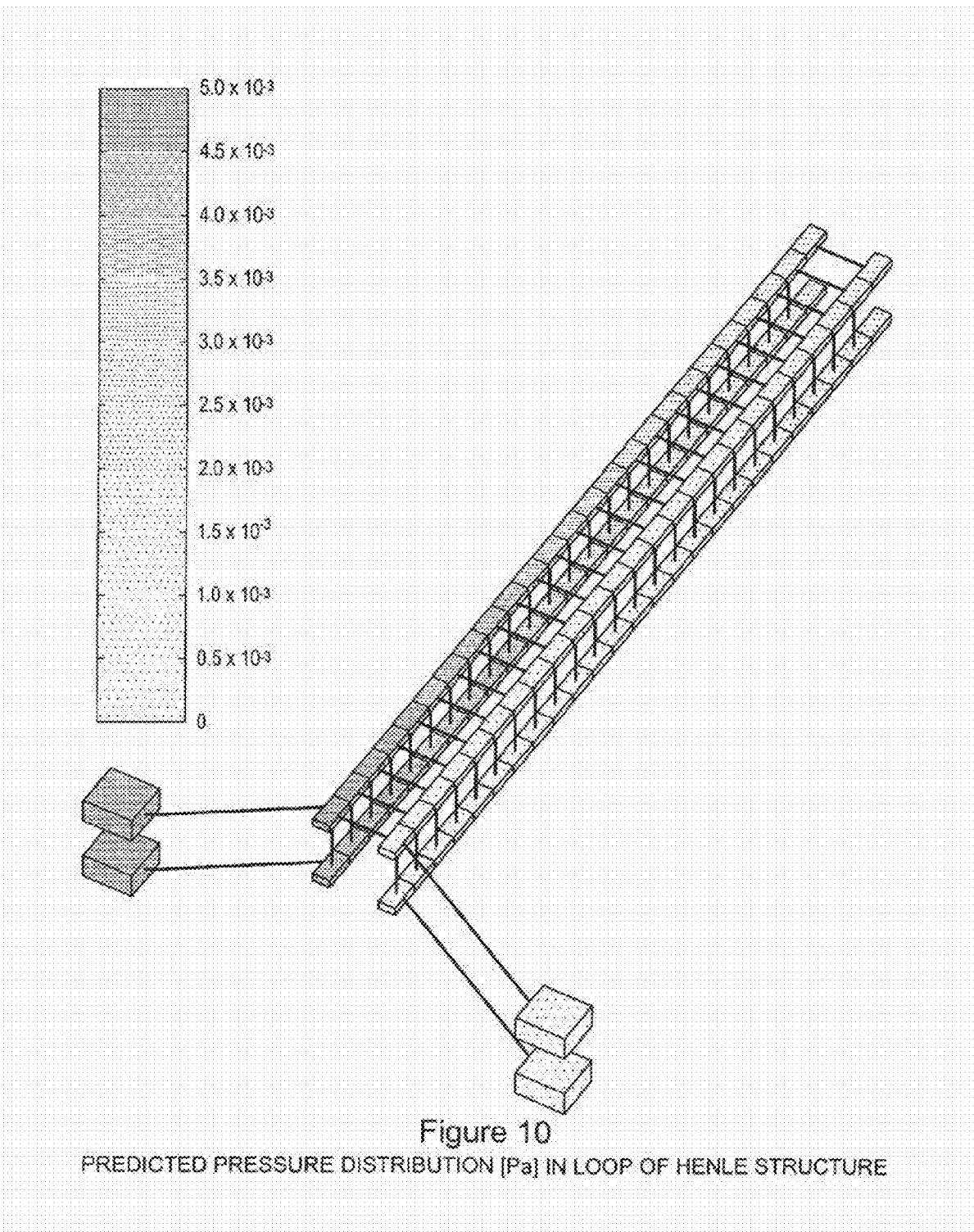
FIG. 10 shows the predicted pressure distribution in a microfabricated bioartificial Loop of Henle structure according to an illustrative embodiment of the invention.
Figure 11:
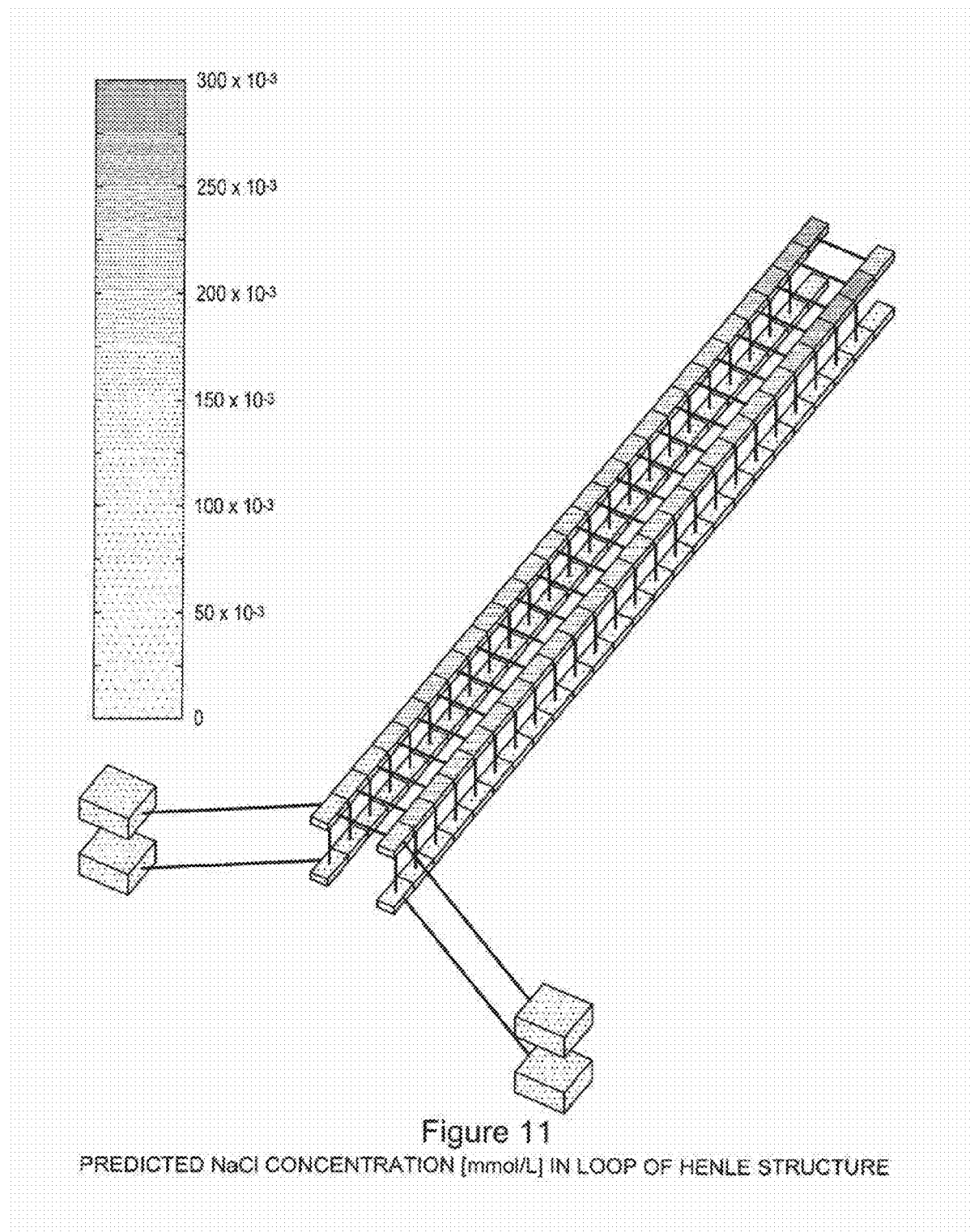
FIG. 11 shows the predicted NaCl concentration in a microfabricated bioartificial Loop of Henle structure according to an illustrative embodiment of the invention.

A schematic of a simulated geometry of the Loop of Henle, according to one approach, is shown in FIG. 9. Predicted distributions of pressure and concentration of NaCl are shown in FIGS. 10 and 11, respectively. A dimensioned drawing of an illustrative bioartificial Loop of Henle structure, according to the invention, is shown in FIG. 12. According to one feature, the structure shown in FIG. 12 may be employed for either a blood or filtrate loop.

According to one approach, calculated dimensions structure of FIG. 12 that yield desired concentration behavior in both the blood and filtrate loops are $T_{loop} \approx 100$ μm, $W_{loop} \approx 300$ μm, $D_{loop} \approx 100$ μm, $L_{loop} \approx 3$ cm, and a membrane thickness of about 100 μm. It is understood that these dimensions may be changed to accommodate cells whose behavior does not exactly match the assumed behavior, without departing from the scope of the invention.

Distal Tubule

Figure 7A:
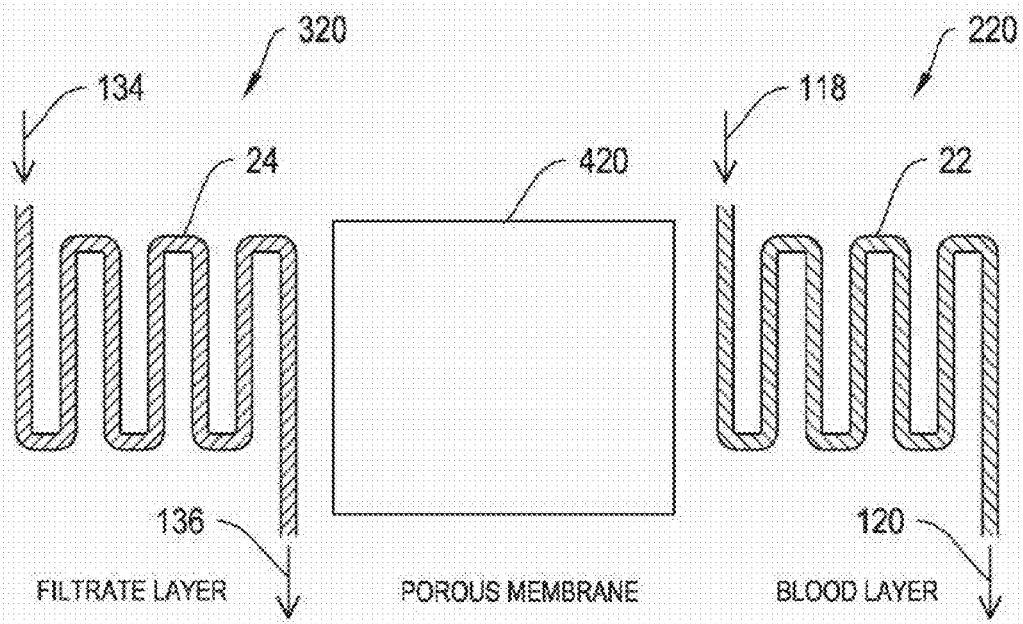
FIG. 7A is schematic of unassembled layers of a microfabricated bioartificial distal tubule according to an illustrative embodiment of the invention.
Figure 7B:
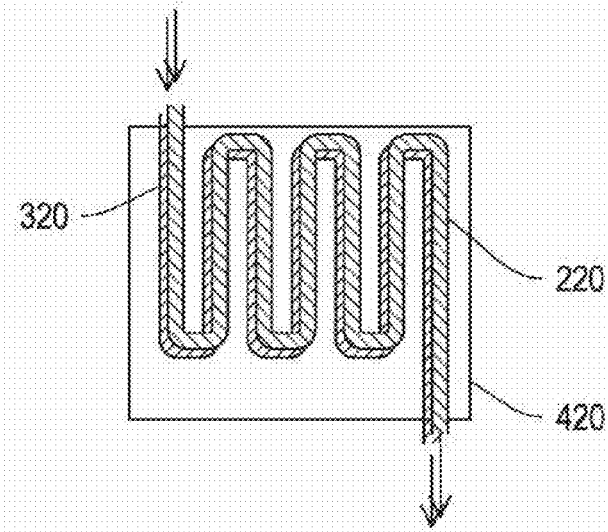
FIG. 7B is a schematic of assembled layers of a microfabricated bioartificial distal tubule according to an illustrative embodiment of the invention.

The primary function of the distal tubule is to allow water to move by osmosis from the filtrate to the blood. It also provides a large area for transport. FIGS. 7A and 7B shows a bioartificial distal tubule 20 according to an illustrative embodiment of the invention. As shown, the bioartificial distal tubule 20 of FIG. 7A or 7B is similar in construction to the bioartificial Loop of Henle 10 of FIGS. 3-5 in that it includes a filtrate layer 320 and a blood flow layer 220 separated by a porous or semi-permeable membrane 420. The two layers 320 and 220 are aligned so as to allow transport from one layer to the other.

As illustrated in FIGS. 7A and 7B, the filtrate layer 320 includes a substantially serpentine microchannel 24 having a filtrate inlet 134 and a filtrate outlet 136, which carries the filtrate flow through the distal tubule 20. When the distal tubule 20 is part of the integrated device 100 as shown in FIG. 2 and connected with the bioartificial loop 10 as shown in FIG. 3, the filtrate inlet 134 is in fluid communication with the filtrate outlet 132 of the loop 10.

As illustrated in FIGS. 7A and 7B, the blood layer 220 includes a substantially serpentine microchannel 22 having a blood inlet 118 and a blood outlet 120. As shown in FIG. 2, the blood flows out of the integrated device 100 through the blood outlet 120 of distal tubule.

In certain embodiments, the filtrate layer 320 can be lined with water-permeable cells to allow water to exit from the filtrate layer 320 and enter the blood flow layer 220, but not solutes or other molecules. The filtrate side of the distal tubule is connected to the filtrate side of the Loop of Henle, but otherwise the tubule does not have to be located near the Loop of Henle (or the collecting duct), and thus may be located in the same device or in a separate but connected device.

According to one approach, the same mass transfer parameters are used for the distal tubule as for the Loop of Henle. A dimensioned drawing of a bioartificial distal tubule according to an illustrative embodiment of the invention is shown in FIG. 13. According to the illustrative embodiment, the structure depicted in FIG. 13 may be employed as either a blood or filtrate loop. According to one illustrative implementation, a distal tubule with the dimensions $W_{distal} \approx 100$ μm, $D_{distal} \approx 100$ μm, $L_{distal} \approx 4$ cm is employed for both the blood and filtrate loops to achieve necessary re-absorption of water from the filtrate. However, as discussed above with respect to the Loop of Henle, any suitable dimensions may be employed without departing from the scope of the invention.

Collecting Duct

Figure 8A:
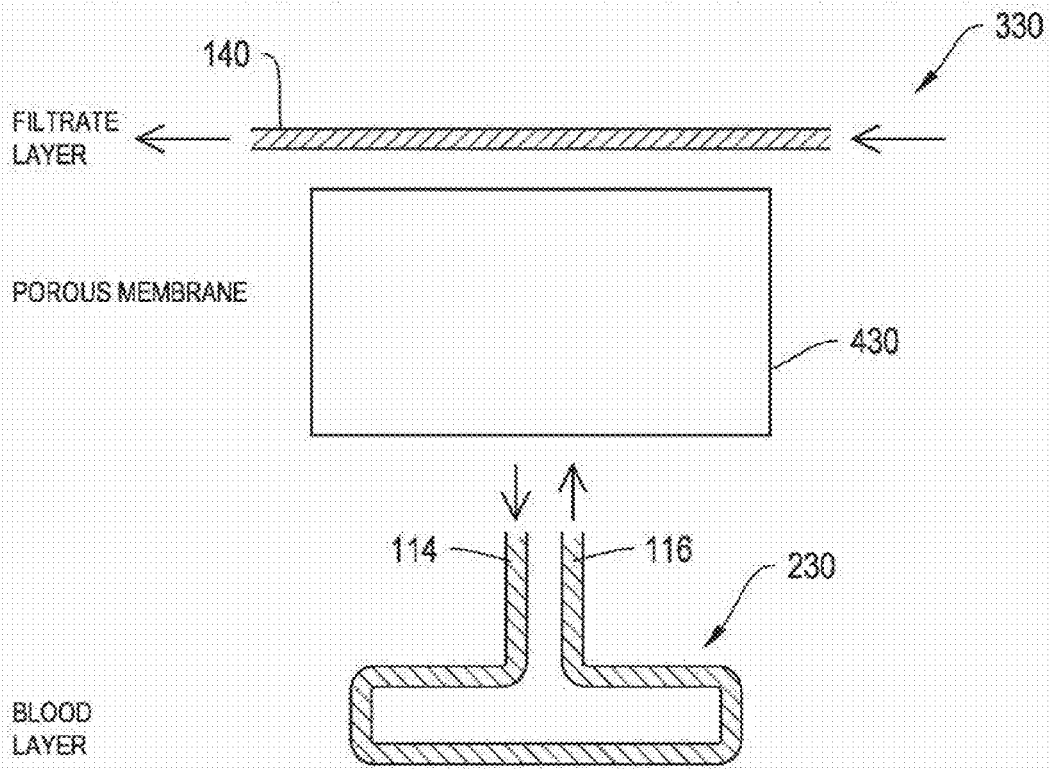
FIG. 8A is schematic of unassembled layers of a microfabricated bioartificial collecting duct according to an illustrative embodiment of the invention.
Figure 8B:
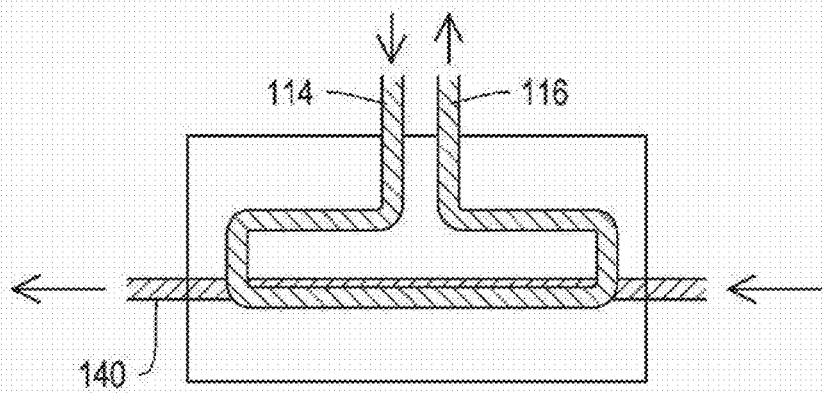
FIG. 8B is a schematic of assembled layers of a microfabricated bioartificial collecting duct according to an illustrative embodiment of the invention.

The primary function of the collecting duct is to allow water to move by osmosis from the collecting duct and to keep other solutes in, thus creating highly concentrated urine. According to one embodiment as illustrated in FIGS. 8A and 8B, similar to the previous two components of the integrated device 100, the bioartificial collecting duct 30 includes a filtrate layer 330 and a blood flow layer 230 separated by a porous membrane 430. Each of the filtrate layer 330 and the blood flow layer 230 includes a microfluidic channel or microchannel to allow the respective fluid to flow through. The filtrate layer 330 can also be lined with water-permeable cells.

As illustrated in FIGS. 3 and 6, blood flows into the bioartificial loop 10 from the blood inlet 110 of the descending limb 12 to the blood outlet 112 of the ascending limb 14. As illustrated in FIG. 2, the collecting duct 30 is connected to the loop 10 in these locations, in that, the blood inlet 114 of the collecting duct 30 shown in FIG. 8 is in fluid communication with the blood outlet 112 of the loop 10 in the integrated device 100. However, the collecting duct 30 does not have to be in physical proximity to the bioartificial Loop of Henle 10, so the two components can exist in separate but connected devices. The blood then flows through and out of the collecting duct 30 from the blood outlet 116, which is in fluid communication with the blood inlet 118 of the distal tubule (as shown in FIGS. 7A and 7B) in the integrated device 100 (as shown in FIG. 2).

As illustrated in FIGS. 7A and 7B, the filtrate flows into the distal tubule 20 from the filtrate inlet 134 (in fluid communication with the filtrate outlet 132 of the loop 10 in the integrated device 100) to the filtrate outlet 136. As shown in FIGS. 8A and 8B, the filtrate flows through and out of the collect duct from the filtrate outlet 140, which also services the filtrate outlet of the integrated device 100 (as shown in FIG. 2).

According to one approach, the same mass transfer parameters are used for the distal tubule as for the previous structures. FIG. 14 shows a dimensioned drawing of collecting duct according to an illustrative embodiment of the invention. As shown, the collecting duct of FIG. 14 has dimensions of $D_{duct} \approx 100$ μm, $W_{duct} \approx 100$ μm, $L_{duct} \approx 2$ cm to achieve the desired production of concentrated urine. However, as in the case of the Loop of Henle and the distal tubule, the collecting duct may employ any suitable dimensions without departing from the scope of the invention.

Accordingly, various devices and systems that can mimic the function of a kidney or various components of a kidney are provided herein. In particular, an integrated device may substantially replicate the function of a nephron unit and has bioartificial components that mimic the function of various components of a nephron unit.

In certain embodiments, a bioartificial system that mimics the function of a kidney may comprise a plurality of the integrated device 100 as shown in FIG. 2. For example, a system of the invention may comprise 1, 10, 100, 1000, 10000, 100000, 1000000, or more units of the integrated device 100. The system can be substantially bi-layer or include multiple, stacked bi-layer units of the integrated device. Such a bioartificial system may be implanted into a subject patient in need thereof, and an implantable system is preferably made or coated with one or more biocompatible materials. A bioartificial system of the invention may also be suitable for excorporeal use by a subject patient in need thereof.

A bioartificial system of the invention that mimics kidney function may or may not function at the same level as a natural, healthy kidney. But a bioartificial system of the invention preferably replicates kidney function at a level that can alleviate the subject patient's conditions or diseases involving kidney dysfunction. The kidney or nephron function level can be determined by one or more tests. For example, the National Kidney Foundation recommends three simple tests to screen for kidney disease: a blood pressure measurement, a spot check for protein or albumin in the urine (proteinuria), and a calculation of glomerular filtration rate (GFR) based on a serum creatinine measurement. Measuring urea nitrogen in the blood provides additional information. A GFR of 90 or above is typically considered normal (e.g., 100% function level). Kidney damage is associated with mild decrease in GFR (60 to 89). A moderate decrease in GFR usually ranges from 30 to 59). A severe reduction in GFR is indicated with a GFR from 15 to 29. Kidney failure is determined by a GFR of less than 15. Accordingly, a bioartificial system of the invention that replicates kidney function may restore a subject patient's GFR from less than 15 to above 30, 50, 60, 70, 80, and most preferably above 90.

Methods for Making the Devices and Systems of the Invention

Microfabrication

According to a further aspect of the invention, an integrated device such as depicted in FIG. 2 is fabricated with the desired dimensions and having a permeable membrane between layers using MEMS technology. Disclosure regarding illustrative approaches that may be employed with the structures of the invention are disclosed in the following references, the contents of which are incorporated herein by reference in their entirety: U.S. Pat. Nos. 6,942,879; 6,455,311, and U.S. Patent Application Publication Nos. 20060136182, 20050238687, 20050202557, 20030003575, 20020182241. There are numerous ways to incorporate a porous membrane between the bioartificial components of the invention.

In certain embodiments, the invention provides a method for forming a bioartificial system that replicates kidney function comprising the steps of: stacking a plurality of a bi-layer unit comprising a) a first layer defining upper and lower surfaces, wherein at least one surface of the first layer includes microchannels formed therein to allow blood to flow through; b) a second layer defining upper and lower surfaces, wherein at least one surface of the second layer includes microchannels formed therein to allow filtrate to flow through; c) a semi-permeable or porous membrane defining an upper surface and a lower surface, wherein the upper surface of the membrane is secured adjacent to the lower surface of the first layer and the lower surface of the membrane is secured adjacent to the upper surface of the second layer. Methods for forming such a bi-layer unit is described in detail in, e.g., U.S. Patent Application Publication No. 20050202557.

In specific embodiments, a method of the invention further comprises forming a microfluidic network by interconnecting the stacked bi-layers with vertical links. Methods for forming such a three-dimensional microfluidic network is described in detail in, e.g., U.S. Patent Application Publication No. 20060136182.

The methods may include using one or more molds. A "mold" is a device on the surface of which the structure of the microchannels is etched or formed. Fabrication of a mold begins by selection of an appropriate substrate. The choice of a substrate material is guided by many considerations, including the requirements placed on the fabrication process by the desired mold dimensions, the desired size of the ultimate template, and the surface properties of the wafer and their interaction with the various cell types, extracellular matrix ("ECM") and polymeric backbone. Also important are the thermal properties, such as the glass transition temperature (Tg), which must be high enough so that the network of pores in the mold does not collapse upon solvent removal.

Molds can be formed from a variety of materials, including, but not limited to, inert materials such as silicon, polymers such as polyethylene vinyl acetate, polycarbonate, and polypropylene, and materials such as a ceramic or material such as hydroxyapatite. In particular, the mold can be formed from metals, ceramics, semiconductors, organics, polymers, and composites. These materials are either inherently suitable for the attachment and culture of animal cells or can be made suitable by coating with materials described herein to enhance cell attachment and culture (e.g. gelatin, matrigel, vitrogen and other tissue culture coatings known in the art) for cellularized components described herein.

In certain embodiments, MEMS replica molding can be used to make a "polymer scaffold" for seeding cells. In this method, a mold is made as described herein, for example, of silicon, and is then used as a template on which a polymeric material is cast. The polymer scaffold can then be peeled away from the mold and seeded with cells.

Properties of the mold and/or polymer scaffold surface can be manipulated through the inclusion of materials on the mold or in polymer scaffold material which alter cell attachment (for example, by altering the surface charge or structure), porosity, flexibility or rigidity (which may be desirable to facilitate removal of tissue constructs). Moreover, advances in polymer chemistry can aid in the mechanical tasks of lifting and folding as well as the biologic tasks of adhesion and gene expression.

In certain embodiments, mold and/or polymer scaffold pieces are fitted together. In certain embodiments, at least a portion of the mold or polymer scaffold pieces are separated by a semi-permeable membrane.

Molds can be made by creating small mechanical structures in silicon, metal, polymer, and other materials using microfabrication processes. These microfabrication processes are based on well-established methods used to make integrated circuits and other microelectronic devices, augmented by additional methods developed by workers in the field of micromachining.

Microfabrication processes that can be used in making the molds disclosed herein include lithography; etching techniques, such as lasers, plasma etching, photolithography, or chemical etching such as wet chemical, dry, and photoresist removal; or by solid free form techniques, including three-dimensional printing (3DP), stereolithography (SLA), selective laser sintering (SLS), ballistic particle manufacturing (BPM) and fusion deposition modeling (FDM); by micromachining; thermal oxidation of silicon; electroplating and electroless plating; diffusion processes, such as boron, phosphorus, arsenic, and antimony diffusion; ion implantation; film deposition, such as evaporation (filament, electron beam, flash, and shadowing and step coverage), sputtering, chemical vapor deposition (CVD), epitaxy (vapor phase, liquid phase, and molecular beam), electroplating, screen printing, lamination or by combinations thereof. See Jaeger, Introduction to Microelectronic Fabrication (Addison-Wesley Publishing Co., Reading, Mass. 1988); Runyan, et al., Semiconductor Integrated Circuit Processing Technology (Addison-Wesley Publishing Co., Reading, Mass. 1990); Proceedings of the IEEE Micro Electro Mechanical Systems Conference 1987-1998; Rai-Choudhury, ed., Handbook of Microlithography, Micromachining & Microfabrication (SPIE Optical Engineering Press, Bellingham, Wash. 1997). The selection of the material that is used as the mold determines how the surface is configured to form the branching structure.

The design of the microfluidic channels or microchannels in the mold can be constructed by a number of means, such as fractal mathematics, which can be converted by computers into two-dimensional arrays of branches and then etched onto wafers. Also, computers can model from live or preserved organ or tissue specimens three-dimensional vascular channels, convert to two-dimensional patterns and then help in the reconversion to a three-dimensional living vascularized structure. Techniques for producing the molds include techniques for fabrication of computer chips and microfabrication technologies. Other technologies include laser techniques.

The designs of the present invention may comprise stacked, folded or rolled series of two-dimensional layers, with the two-dimensional layers arranged such that large numbers of interconnection points exists between layers. Each two-dimensional layer is generated by using a computational fluid dynamic (CFD) model, which produces a model network to simulate the critical structure and function of the tissue or organ of interest. The CFD model generates multiple, preferably at least two, distinct two-dimensional layers, which are arranged to allow for a very large number of vertical interconnects between layers.

Cell Seeding

In specific embodiments, a method of the invention further comprises introducing to the microchannels that allow filtrate to flow through renal epithelial cells, such as for example, water-permeable cells or salt-pumping cells.

In specific embodiments, a method of the invention further comprises introducing to the microchannels that allow blood to flow through vascular cells, such as for example, endothelial cells.

A structure comprising joined or fastened molds and/or polymer scaffolds, with or without a semi-permeable membrane between them, is also termed an "apparatus." Sets of cells can be added to or seeded into the three-dimensional apparatus, which can serve as a template for cell adhesion and growth by the added or seeded cells. The added or seeded cells can be water-permeable cells or salt-pumping cells. A second set of cells, such as endothelial cells, can be added to or seeded onto the assembled apparatus through other vessels (i.e., those microchannels in the blood flow layers) than those used to seed the first set of cells. The cell seeding is performed by slow flow. The geometry of the apparatus will typically determine the flow rates. In general, endothelial cells can enter and form blood vessel walls in micromachined channels that are about 10-50 microns in diameter or depth. Thus, in addition to serving as a mechanical framework for the organ, the assembled apparatus provides a template for all of the microstructural complexity of the organ, so that cells have a mechanical map to locate themselves and form subsystems, such as the water-permeable cells for the thinner descending limb and the salt-pumping cells for the thicker ascending limb of the Loop of Henle.

Optionally, functional cells are seeded into both a first and second mold and/or polymer scaffold with microchannels on their surfaces, and the two molds and/or polymer scaffolds are joined or fastened with a semi-permeable or porous membrane between them, allowing gas exchange, diffusion of nutrients, and waste removal. One layer comprises the circulation through which blood, plasma or media with appropriate levels of oxygen can be continuously circulated to nourish the second layer. The second layer comprises a reservoir for the functional cells of a nephron, and includes inlets and outlets for urine or filtrate flow. This results in an apparatus for making tissue lamina, wherein each of the first and second molds and/or polymer scaffolds and the semi-permeable membrane are comprised of material that is suitable for attachment and culturing of animal cells.

Cell Culture

According to one embodiment, the renal countercurrent system requires cell activity to function. In the ascending tubule, cells that pump salt out and block other constituents of the tubule are required. In other parts of the device, cells that allow water through but block other constituents are required.

Salt-Pumping Cells

The natural thick ascending tubule is typically lined with cells that have a number of functions. According to one embodiment to create a high concentration at the tip of the bioartificial Loop of Henle, important functions are the ability to pump salt out of the tubule and the ability to keep other constituents, including water. These functions are achieved following the methods described in the literature, such as for example in Bourgeois, et al. Differentiated thick ascending limb (TAL) cultured cells derived from SV40 transgenic mice express functional apical NHE2 isoform: effect of nitric oxide, *Eur J Physiol*. (2003) 446:672-683. Some literature shows that the required cells can be cultured from rat or mouse kidney or obtained from commercial vendors. The cells can be immortalized and induced to proliferate and demonstrate salt-pumping (and other functions) by standard cell culture techniques.

Water-Permeable Cells

According to one embodiment of the invention, the descending tubule, distal tubule, and collecting duct are coated with cells that allow water to pass through while blocking other constituents for the device to function properly. A number of research groups have demonstrated culture and function of these cells using standard cell culture techniques. See, e.g., Zhang, et al. Proliferation and osmotic tolerance of renal inner medullary epithelial cells in vivo and in cell culture, *Am J Physiol Renal Physiol*. (2002)283: F302-F308., Schumacher, et al. Advanced technique for long term culture of epithelia in a continuous luminal-basal medium gradient. *Biomaterials* (2002) 23:805-815. Both types of cells are readily cultured and prompted to function, and thus can provide the necessary functions for this device.

It should be noted that Applicants consider all operable combinations disclosed herein, including in the references cited herein, to be claimable as potentially patentable subject matter.

All references cited herein are incorporated by reference in their entirety.

We claim:

1. A device replicating kidney function comprising:
   a microfabricated blood flow layer having a first microfluidic channel formed therein for carrying blood, the first microfluidic channel including a loop, and wherein portions of the loop in the first microfluidic channel are separated by a porous medium;
   a microfabricated filtrate layer having a second microfluidic channel formed therein for carrying a filtrate flow, the second microfluidic channel including a loop; and
   a permeable membrane positioned between the blood flow layer and the filtrate layer coupling the blood flow layer to the filtrate layer.

2. The device of claim 1, wherein the microfabricated blood flow layer substantially overlaps with the microfabricated filtrate layer, allowing analytes in the blood in the microfabricated blood flow layer to filter through the permeable membrane into the filtrate flow in the microfabricated filtrate layer.

3. The device of claim 1, wherein the second microfluidic channel is generally u-shaped.

4. The device of claim 1, wherein the microfabricated blood flow layer comprises a blood inlet.

5. The device of claim 1, wherein the microfabricated filtrate layer comprises a filtrate inlet.

6. The device of claim 1, wherein the first microfluidic channel includes an ascending limb and a descending limb.

7. The device of claim 1, wherein the second microfluidic channel includes an ascending limb and a descending limb.

8. The device of claim 6, wherein the porous medium is deposited between at least a portion of the ascending limb and the descending limb of the first microfluidic channel.

9. The device of claim 1, wherein the porous medium comprises a wall having a plurality of passageways coupling the first microfluidic channel to the second microfluidic channel, formed therein for allowing fluid flow between the portions of the loop separated by the wall.

10. The device of claim 1, comprising a collecting duct, wherein the collecting duct comprises:
    a collecting duct blood flow layer, which includes the portion of the first microfluidic channel that forms a loop;
    a collecting duct filtrate layer, which includes a portion of the second microfluidic channel; and
    a second porous membrane positioned between the collecting duct blood flow layer and the collecting duct filtrate layer.

11. The device of claim 10, wherein the microfabricated blood flow layer comprises the collecting duct blood flow layer.

12. The device of claim 10, wherein the collecting duct filtrate layer comprises a filtrate outlet.

13. The device of claim 1 comprising a distal tubule, wherein the distal tubule comprises:
    a distal tubule blood flow layer, which includes a portion of the first microfluidic channel;
    a distal tubule filtrate layer, which includes a portion of the second microfluidic channel; and
    a third porous membrane positioned between the distal tubule blood flow layer and the distal tubule filtrate layer.

14. The device of claim 13, wherein the microfabricated blood flow layer comprises the distal tubule blood flow layer.

15. The device of claim 13, wherein the microfabricated filtrate layer comprises the distal tubule filtrate layer.

16. The device of claim 13, wherein the first microfluidic channel in the distal tubule blood flow layer is a generally serpentine microchannel and the second microfluidic channel in the distal tubule filtrate layer is a generally serpentine microchannel.

17. The device of claim 16, wherein the distal tubule provides for diffusion of water from the second microfluidic channel in the distal tubule filtrate layer across the third porous membrane into the first microfluidic channel in the distal tubule blood flow layer.

18. The device of claim 16, wherein a distal end of the second microfluidic channel in the distal tubule filtrate layer couples to a collecting duct.

19. The device of claim 16, wherein a distal end of the first microfluidic channel in the distal tubule blood flow layer comprises a blood outlet.

20. The device of claim 1, comprising a second microfabricated blood flow layer and a second microfabricated filtrate layer substantially similar to the microfabricated blood flow layer and the microfabricated filtrate layer.

21. The device of claim 20, wherein the second microfabricated blood flow layer and the second microfabricated filtrate layer are coupled to the microfabricated blood flow layer and the microfabricated filtrate layer.

22. The device of claim 21, wherein the second microfabricated blood flow layer and the second microfabricated filtrate layer are coupled to the microfabricated blood flow layer and the microfabricated filtrate layer via one or more vertical links formed in one of the blood flow layer and the filtrate layer.

* * * * *